US010293095B2

(12) United States Patent  
Elliott

(10) Patent No.: US 10,293,095 B2  
(45) Date of Patent: May 21, 2019

(54) HYPEROXYGENATION/HYPERTHERMIA TREATMENT APPARATUS

(71) Applicant: Jerry Chris Elliott, Oklahoma City, OK (US)

(72) Inventor: Jerry Chris Elliott, Oklahoma City, OK (US)

(*) Notice: Subject to any disclaimer, the term of this patent is extended or adjusted under 35 U.S.C. 154(b) by 0 days.

(21) Appl. No.: 15/710,022

(22) Filed: Sep. 20, 2017

(65) Prior Publication Data

US 2018/0008762 A1 Jan. 11, 2018

Related U.S. Application Data

(63) Continuation-in-part of application No. 14/329,346, filed on Jul. 11, 2014, now abandoned.

(51) Int. Cl.
*A61M 1/36* (2006.01)
*A61M 1/32* (2006.01)
*A61M 1/02* (2006.01)

(52) U.S. Cl.
CPC ......... *A61M 1/36* (2013.01); *A61M 1/32* (2013.01); *A61M 1/369* (2013.01); *A61M 1/0281* (2013.01); *A61M 2202/0208* (2013.01); *A61M 2202/0216* (2013.01); *A61M 2205/3653* (2013.01); *A61M 2205/583* (2013.01)

(58) Field of Classification Search
CPC .... A61M 1/16; A61M 1/1678; A61M 1/1698; A61M 1/369
See application file for complete search history.

(56) References Cited

U.S. PATENT DOCUMENTS

| | | | | |
|---|---|---|---|---|
| 3,856,475 | A * | 12/1974 | Marx | A61M 1/1698 128/DIG. 3 |
| 4,280,981 | A * | 7/1981 | Harnsberger | A61M 1/325 422/46 |
| 5,124,127 | A * | 6/1992 | Jones | A61M 1/1698 128/DIG. 3 |
| 9,408,959 | B2 * | 8/2016 | Gourlay | A61M 1/1698 |
| 2003/0039582 | A1 * | 2/2003 | Chambers | A61M 1/1678 422/44 |
| 2004/0022669 | A1 * | 2/2004 | Ruan | A23L 3/26 422/22 |

(Continued)

*Primary Examiner* — Benjamin J Klein
(74) *Attorney, Agent, or Firm* — James Robert Johnson

(57) ABSTRACT

The described invention is a hyperthermia and hyperoxygenation medical apparatus for treating diseases of the blood and purification of stored blood supplies. The invention comprises a hollow chamber through which blood is made to flow. Within the hollow chamber are a heating element and a gas diffuser. As blood flows through the chamber, blood is heated to a preset limit while ozone or other beneficial gas is diffused into the blood by a diffuser with pores to a preset concentration. After heating and gasification, blood exits the hollow chamber and is either returned to the patient or returned to storage. The hollow chamber, heating element and gas diffuser are designed to maintain efficient, linear blood flow through the invention, in part by taking advantage of die radial symmetry of the hollow chamber and diffuser designs. Linear flow ensures uniform and controlled heating and gasification of the blood with negligible undesirable turbulence to the blood components.

4 Claims, 8 Drawing Sheets

(56) References Cited

U.S. PATENT DOCUMENTS

2010/0274170 A1* 10/2010 Carpenter .......... A61M 1/1698
604/6.09
2016/0008525 A1* 1/2016 Elliot ...................... A61M 1/32
424/529

* cited by examiner

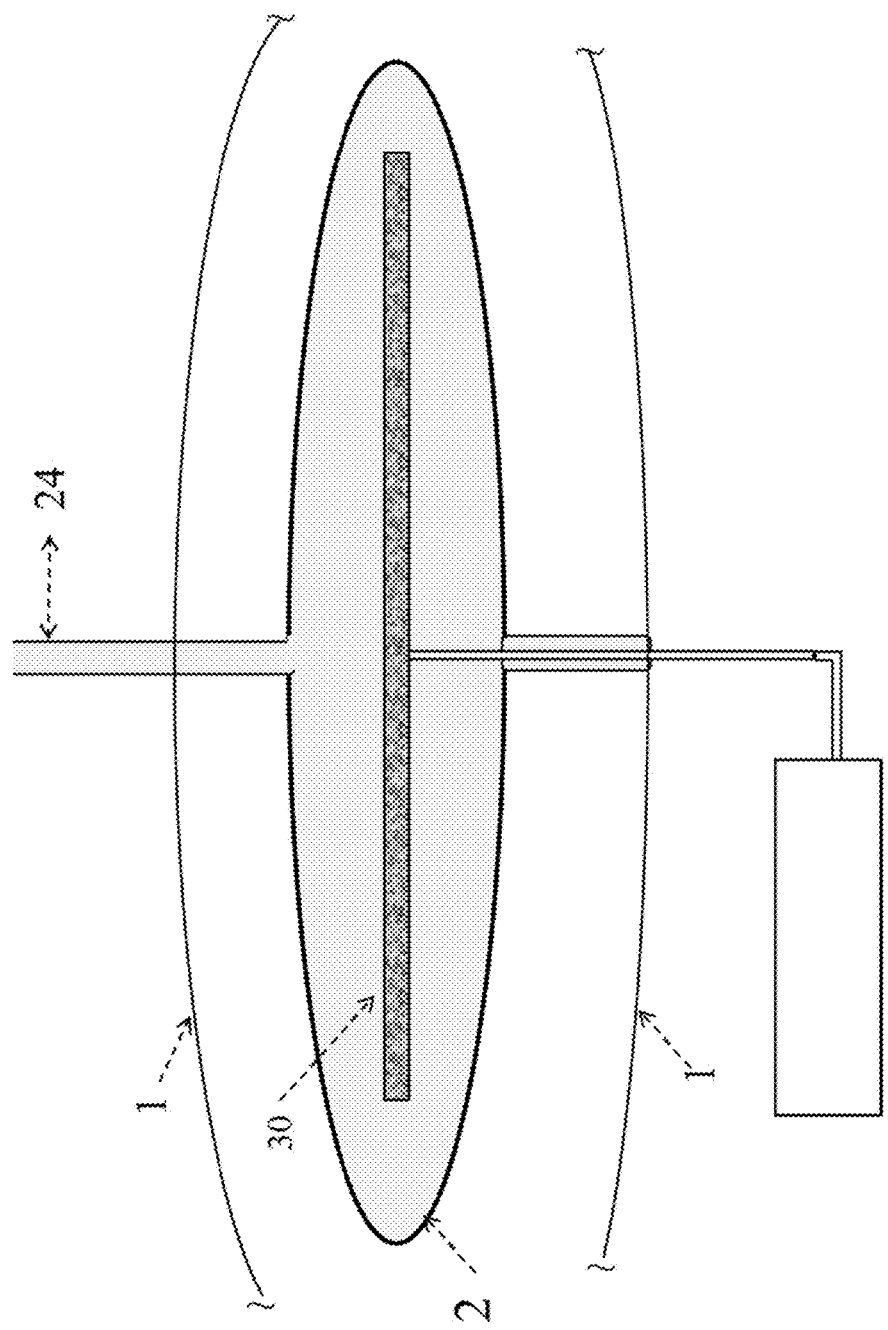

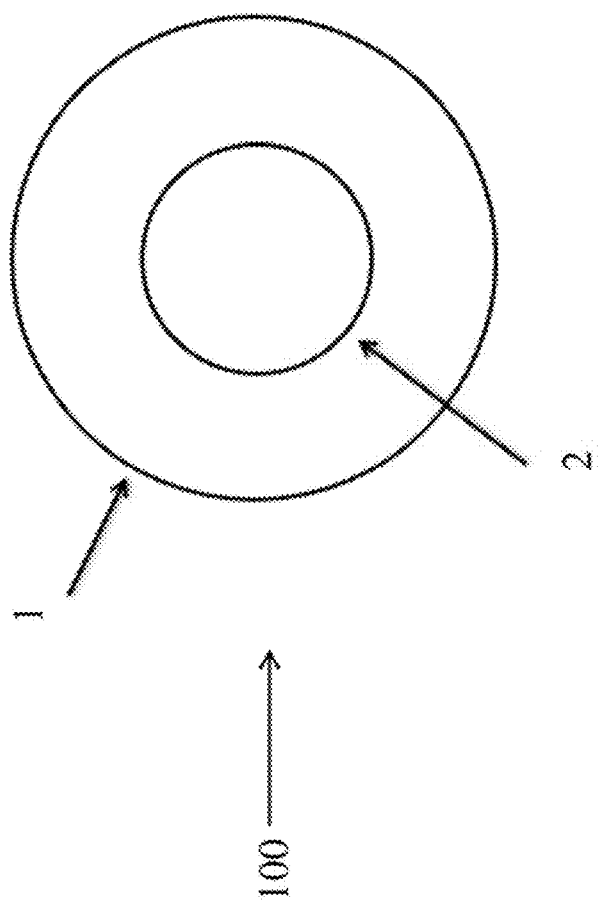

HYPEROXYGENATION/HYPERTHERMIA TREATMENT APPARATUS

This invention claims the benefit of the filing date of a prior non-provisional patent application, U.S. Ser. No. 14/329,346.

BACKGROUND OF THE INVENTION

The general field of the invention is the treatment of illnesses and diseases of the blood and/or body organs by the application of the combination of hyperoxygenation and hyperthermia. The invention is a new apparatus that 1) aids medical research, 2) kills viruses and disease organisms in the blood and 3) purifies stored blood supplies and contaminated blood by the application of hyperoxygenation and hyperthermia to kill pathogens or other harmful cells therein. In this specification, the word "pathogen" refers generally to viruses, bacteria or other microorganisms in the blood capable of causing disease or other health problems. "Harmful cells" includes cancer cells, or other harmful organisms.

Although devices have been devised which can warm or oxygenate the blood for specific tasks, such as to maintain sufficient oxygen in the blood and vital functions to support the life of a patient undergoing open heart surgery or to help warm the patient by the use of warmed blood, at present, no prior art methods or devices suitable to perform the functions of this invention are known to exist to treat and purify blood or stored blood supplies sufficiently to kill pathogens or cancer cells. The difficulty of treating people infected with viruses or who have cancer is well-known. Viruses are notoriously difficult to kill in the body using current medical practices. Likewise, cancer cells have many of the same biological characteristics of other cells in the host body. As a result, what kills the cancer cells may equally kill the patient. Much of cancer research has focused on treating the condition without killing the patient. As a result, much of cancer treatment includes the identification of ways to kill the cancer cells or viruses that minimize harmful effects to the patient.

Devices known to heat and oxygenate the blood are not capable of heating or oxygenating all of the blood sufficiently to kill all of the pathogens or cancer cells in the blood. That is to say, nothing in these devices evidences an ability to raise every portion of the blood passing through the devices to a desired, therapeutic homogenous temperature or to diffuse a sufficient amount of oxygen or ozone into every portion of the blood sufficiently to kill pathogens or harmful cells in the blood. Since these pathogens and cancer cells are capable of reproducing, any device not able to kill all such pathogens and harmful cells cannot be seen to "treat" the blood or the patient. In current devices, pathogens or cancer cells not subjected to sufficient heat or oxygen to kill them simply reproduce. The patient remains ill and affected. In order for a hyperoxygenation/hyperthermia device to function as a treatment device, the flow of blood through the device must ensure all of the blood is subjected to sufficient heat and oxygen levels to kill pathogens and harmful cells. To protect the integrity of blood components and minimize damage to same, among other things, this requires the prevention of eddies or turbulence in the flow of blood, since these flow elements can retain disease-carrying blood that does not pass through the heating or oxygenation elements of the device for the same amount of time as other parts of the flow of blood. Alternately, eddies and turbulence can result in portions of the blood flow remaining too long in the presence of the heating element, resulting in the killing of beneficial blood components.

In the past, hyperthermia and hyperoxygenation have separately been used successfully by medical practitioners and researchers to kill pathogens and harmful cells in the blood. Numerous references cited in the medical field describe the separate use of each of these treatment methods with some success. For various reasons, researchers have been unwilling or unable to perform these treatment methodologies together on patients. This invention allows dual operation of these techniques in a single apparatus in which the flow of blood is sufficiently linear so as to ensure the thorough application of heat and ozone evenly and homogenously to all blood components in the blood flow within the system.

In addition, this invention is a new method for treating patients more safely than using radiation or chemotherapy protocols currently in use and without the undesirable side effects of either. Further, this treatment method is capable of being used in facilities other than hospitals, helping providers control costs while increasing convenience to and comfort of patients. Due to the simplicity, compact design and portability of this invention, treatment may be performed in ambulatory surgical centers, doctors' offices or in the patient's home or other beneficial environments including blood storage units The invention is also a valuable tool suitable for use in medical research combining two known procedures, hyperthermia and hyperoxygenation, in a single delivery device to be used to sterilize human blood to increase the overall potential medical blood supply. With repeated use, the invention may be shown to have a beneficial effect on certain body organs and glands infected with harmful infectious organisms and diseases by its ability to reduce the overall level of infection or disease in the patient. The apparatus is much needed in medical research to determine the beneficial effects of the combination of hyperthermia and hyperoxygenation techniques and treatments, especially on certain types of cancers and blood related diseases.

The device is a helpful research and operational tool to determine the beneficial extent of the combination of hyperoxygenation and hyperthermia to improve erythrocytic metabolism and the reactivity of the immune system with negligible cell damage.

BRIEF SUMMARY OF THE INVENTION

The embodiments described in this specification are exemplary. As such, they are not limiting except as expressly described herein. The invention may be practiced in any form generally permitted by this specification.

It is generally known that many invasive and hostile microorganisms, viruses and cancer cells require lower oxygen levels than the host body's healthy cells typically require. Boosting the oxygen level revitalizes normal cells while killing many viruses, cancer cells and other pathogens. It is also known that controlled temperature elevation can kill viruses, pathogens and cancer cells, while leaving healthy cells unharmed. Ozone gas ($O_3$), for example, has long been recognized as a nonpolluting purification treatment chemical for a range of applications. As an alternative disinfectant to chlorine, ozone has become more widely used as a municipal drinking water disinfectant. The invention consists of and combines two basic and well-known treatment methods, hyperthermia and hyperoxygenation, in an apparatus in which all blood to be treated is equally and thoroughly subjected to hyperthermia and hyperoxygenation. Treatment is not limited to the use of ozone. Throughout this specification, references to ozone should be read to include any form of molecular oxygen, such as $O_2$, known in the field as beneficial to medical treatment.

In order to kill all pathogens or cancer cells in the blood, the invention comprises design elements which optimize flow, primarily by the prevention or minimization of turbulence, eddies or other non-linear flow characteristics. This includes accounting for known flow characteristics of fluids, including blood, such as boundary conditions, primarily edge conditions and flow around an obstruction. For example, it is known that fluid flow in a pipe or tube is subject to boundary conditions-flow is slow against the interior wall of the pipe or tube and faster in the center. At higher rates of flow, the speed differential between the wall and the center can produce to and eddies resulting from shear forces in the fluid. Turbulence or other non-linear flow characteristics retain flow in one location for a longer time than other parts of the flow. In a blood treatment device, this means some portion of the blood is treated to more or less heating and oxygenation than other parts of the blood, depending on whether the non-linear flow occurs near to or away from the treatment area, such as a heating element or oxygenator. As a result of non-linear or turbulent flow, it is either less likely pathogens or cancer cells in the blood are killed of more likely beneficial blood components are harmed. In a device which oxygenates and warms the blood for open heart surgery, for example, this is irrelevant. As long as the blood overall is warm enough and oxygenated enough to maintain life during surgery, treatment of "enough" blood with "enough" oxygen and "enough" warmth is sufficient. However, an attempt to use that type of device to kill pathogens or cancer cells in the blood would leave enough of those harmful cells alive to prevent the patient from being cured. Treatment occurs only when all the treated blood is heated and oxygenated sufficiently to kill pathogens and cancer cells therein. The disclosed invention meets the treatment and patient safety requirements needed in this field.

Equally, the invention incorporates a design in which it uses radial symmetry to ensure control over the heating and oxygenation of the blood.

The invention optimizes and combines the merits of both hyperthermia and hyperoxygenation into a single design for the treatment of viruses, certain types of cancers and the purification of stored blood. By combining these treatment elements, the invention provides an optimized method for killing viruses, cancer cells and other harmful microorganisms. By using the combination of hyperthermia and hyperoxygenation, cells weakened by one form of treatment may then more readily killed by the other. In the invention, hyperthermia and hyperoxygenation occur at the same time and in the same place in the invention. Harmful cells are given no time for recovery or respite. Many harmful cells are killed directly by the application of one of hyperthermia or hyperoxygenation. As to those harmful cells not killed by one of those treatment methods, having been weakened by one treatment element, the harmful cells are more likely to die from the simultaneous or near simultaneous exposure to the other treatment element.

By the combined use of hyperoxygenation and hyperthermia and the ability to ensure equal application of treatment to all portions of the treated blood because of the linear flow characteristics of the blood through the invention, the invention takes advantage of two inherent susceptibilities of disease causing viruses and cells, allowing the application of one treatment method to kill or weaken the subject virus or cell, with the other treatment method killing any surviving pathogens or harmful cells.

After ozone and thermal exposure, different blood cells undergo different trophic, biochemical, and immunological changes that have beneficial effects on people with diseases. Ozone and thermal exposure may kill viruses in blood and accentuate the lysis of infected cells as these become poorly equipped to counteract the action of oxygenation. Oxidation of components on the membrane of Peripheral Blood Mononuclear cells (lymphocytes and monocytes) may also trigger their activation with subsequent release of toxic and possibly dangerous cytokines.

BRIEF DESCRIPTION OF THE DRAWINGS

FIG. 7 depicts another cross-section of the chamber and diffuser in which the heating element is a radiant heating bar disposed within the diffuser.

FIG. 8 depicts a cross section of the preferred embodiment of the chamber and diffuser in which the chamber and diffuser each have a circular cross section.

DETAILED DESCRIPTION OF THE INVENTION

The basic mode of operation of the invention is to heat the blood to a specific, controlled temperature between 105 degrees F. (40.55 degree C.) and 106.7 degrees F. (41.5 degrees C.) while simultaneously hyperoxygenating the blood with ozone or other suitable gas to maximum saturation. In this combination, the high temperature and applied gasification kills or weakens cells and pathogens in the blood susceptible to death at such temperatures. Cells and viruses which are not killed by the high temperature but which are susceptible to high oxygen levels are killed by hyperoxygenation. Similarly, cells and pathogens susceptible to high oxygen levels are killed or weakened by the oxygen levels in the blood. Those cells or viruses not killed by the hyperoxygenation are weakened sufficiently such that they are then killed by the hyperthermic conditions. The blood is then returned to the body. Depending on the patient's illness, the blood may either be cooled before being returned to the body or it may be reintroduced to the body while still warm. Oxygen or ozone diffused into the blood does not typically need to be removed prior to the blood being returned to the patient as they pose no threat to the patient. Hyperthermic/hyperoxygenated blood has the ability to kill pathogens or cancer cells in the body. The design of the invention prevents or minimizes turbulence, eddies and other flow impediments, resulting in even flow past the heating element and hyperoxygenator in a known and controlled manner. As a result, all blood introduced into the invention is heated to a known and controlled temperature and is hyperoxygenated to an equally known and controlled level at an operator controlled rate of flow.

Figure 1:
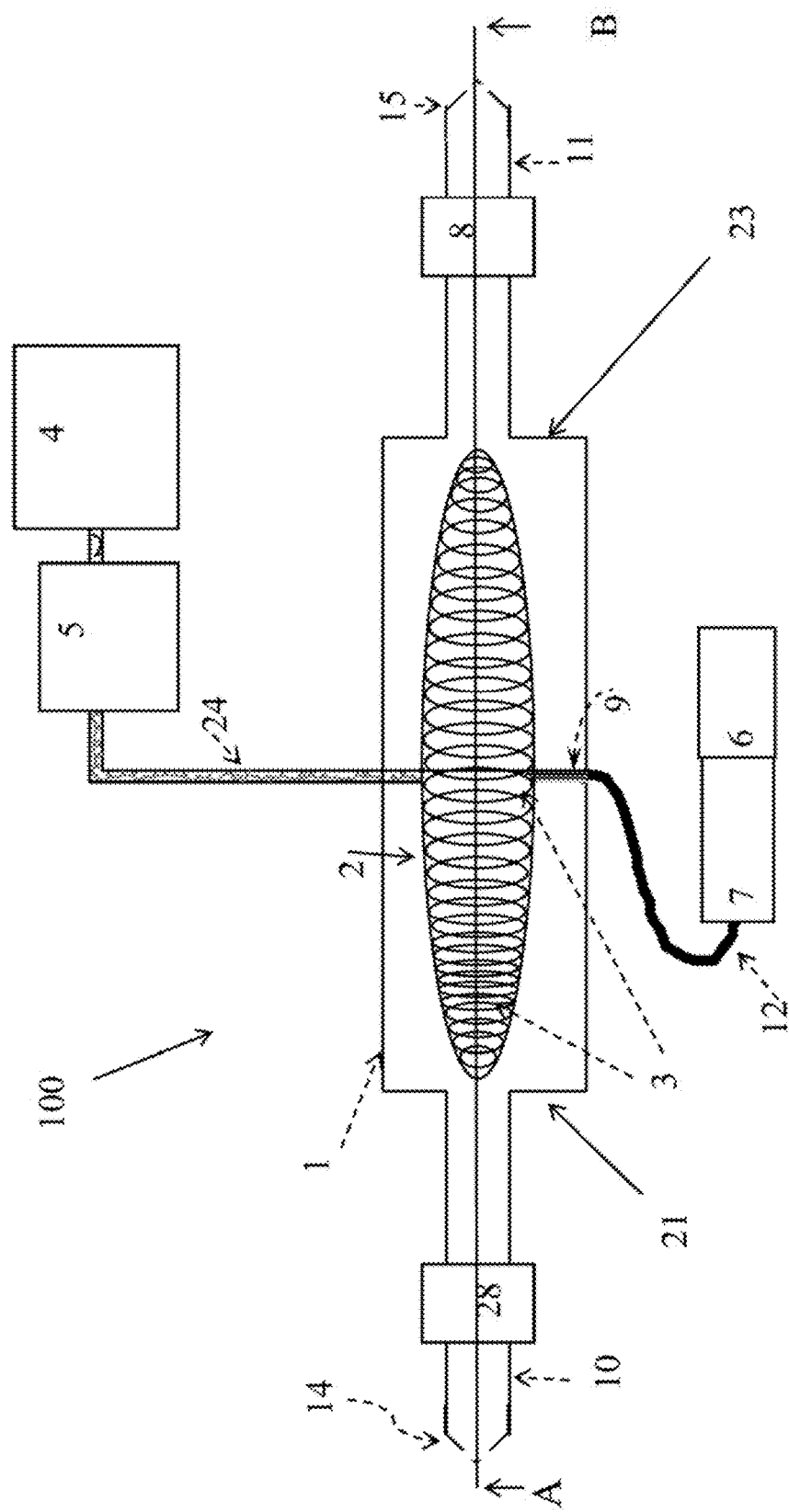
FIG. 1 depicts a representation of the invention showing the preferred embodiment.

Referring first to FIG. 1, a preferred embodiment of the invention is depicted. The patient's blood is drawn from the body through a tube inserted in a patient's vein or artery (not depicted) to the inlet 14 of the invention 100, which fluffier comprises a chamber 1, an ozone diffuser 2 and a heating element 3. As noted, "ozone" is used to refer generally to any molecular oxygen with therapeutic value. Blood is drawn from the patient through any means known in the health care industry for allowing a controlled high rate of blood flow ex vivo such as might be performed for transfusion or dialysis. The line segment AB represents the imaginary longitudinal axis of each of the chamber 1 and diffuser 2.

To obtain the blood from die patient, the patient's blood is drawn and flows into a connecting tube 10. Connecting tube 10 is of approximately the same diameter as the tube carrying blood from the body. To account for fluid flow boundary conditions inside the connecting tube 10, the inner surface of the connecting tube 10 may be coated with a low friction, non-bioreactive coating. Because a small diameter tube increases the likelihood of turbulent or non-linear flow, the low friction coating is used to reduce the amount of shear in the flow. This helps to ensure blood flowing into chamber 1 flows smoothly. The rate of flow into chamber 1 is maintained by use of a pump 28. The design of the pump 28 is such that blood cells and blood components are not damaged by the pump 28 or pumping action. Suitable and commercially available pumps for this are known in the industry. Upon entry into chamber 1, blood temperature is at body temperature (approximately 98.6 degrees F.) or slightly lower, having potentially cooled while passing along the connecting tube 10 and through the pump 28.

Figure 6:
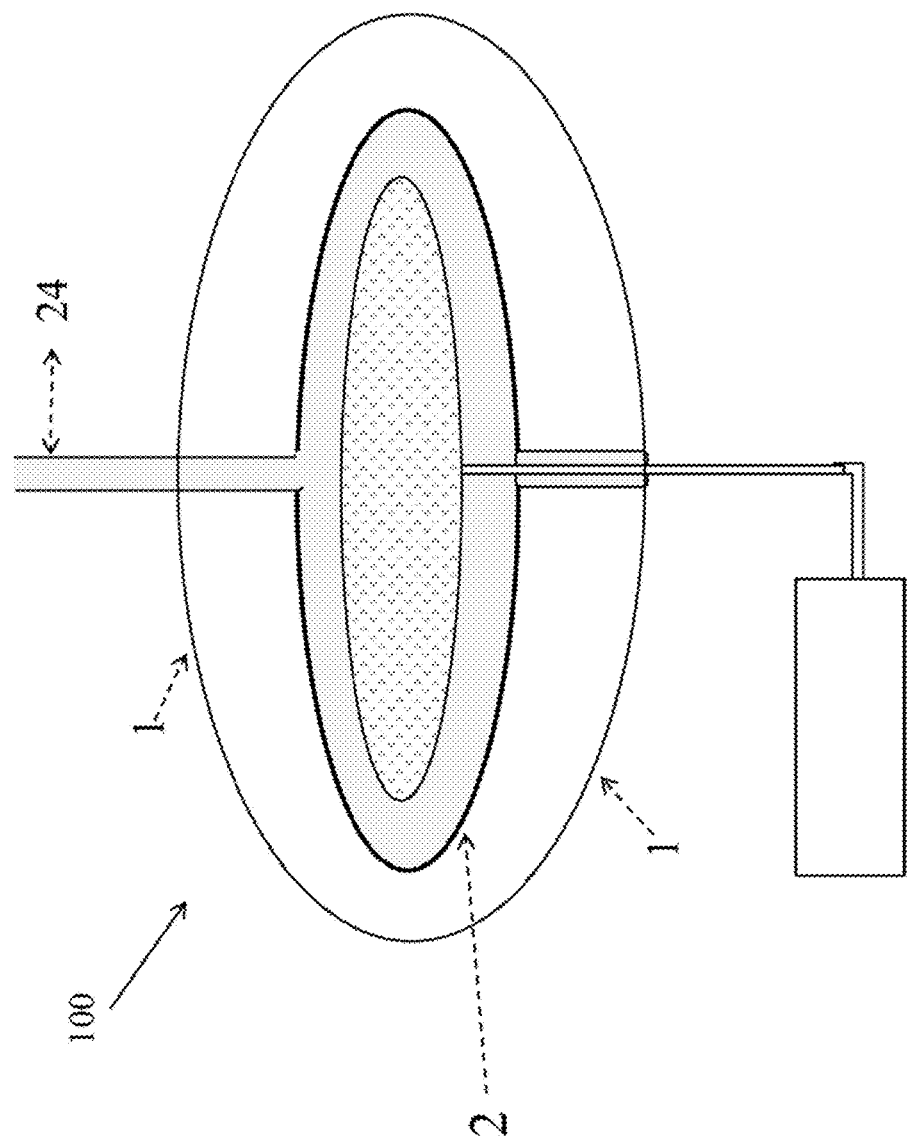
FIG. 6 depicts a cross section of the chamber and diffuser showing that each of the chamber and diffuser has an elliptical cross section.

The connecting tube 10 and chamber 1 are ideally constructed of a clear material, such as glass, plastic or other material which will not react either to heat, oxygen or blood. This permits the operator to view the flow of blood through the invention 100 and to make oxygenation and blood flow adjustments if needed. Flow adjustments are made by speeding up or slowing down the pumping rate of pump 28. As shown more clearly in FIG. 8, in the preferred embodiment chamber 1 is a hollow circular cylinder. In this same preferred embodiment, the diffuser 2 is a hollow, three-dimensional ellipsoid with a circular cross-section. It should be understood that while the preferred embodiment comprises a hollow circular cylinder for the design of the chamber 1 and 3-D ellipsoid for the design of the diffuser 2, the invention is in no way limited to these shapes. The invention 100 may be practiced using any geometry for the chamber 1 and diffuser 2 which permits blood to be pumped through the invention 100 and over or around the heating element 3 and diffuser 2 in a manner which heats and oxygenates all of the blood uniformly. Thus, the chamber 1 may have cylindrical geometry, rectangular geometry or otherwise. It is, however, important for the cross-sectional geometry of the chamber 1 to match the cross-sectional geometry of the diffuser 2 or, if applicable, the heating element 3. The longitudinal axis of the diffuser 2 is positioned to lie directly on the longitudinal axis of the chamber 1. This imposes radial symmetry on the invention 100, which helps to ensure the blood flows through the chamber without turbulence or non-linear flow characteristics. Referring to FIG. 6, in an alternative embodiment of the invention 100, chamber 1 has an elliptical cross-section, as does diffuser 2. As in the preferred embodiment, in the alternative embodiment, the distance between a point on the outer surface of the diffuser 2 and the nearest point on the inner surface of the chamber 1 remains constant or very close to constant. Blood flow is constrained between approximately parallel surfaces, which reduces the likelihood of turbulent or non-linear flow.

Referring again to FIG. 1, chamber 1 has a diameter larger than the diameter of the connecting tube 10, resulting in a reduction of forward velocity of blood flow through the chamber 1. The reduction in the velocity of the blood while in the chamber 1 further reduces the likelihood of turbulence or non-linear flow of the blood through the invention 100. The inner surface of the chamber 1 may also be coated with a low friction, clear, non-bioreactive coating. The combination of the larger cross-sectional area of the chamber 1 as compared to the connecting tube 10 and smooth inner surface means the inner surface boundary conditions are minimized, thus reducing shear forces in the chamber 1. As shown in FIG. 1, the diameter of chamber 1 is approximately three times the diameter of connecting tube 10, although this ratio is not strictly necessary. Flow rate per unit length is proportional to the cross-sectional area through which the fluid flows. In that the specific heat of blood is known, dimensions of the invention 100, such as diameter and length, and likewise dimensions of the diffuser 2 may be determined by calculation based on the characteristics of the pathogens or harmful cells sought to be killed. For clarity, there is no single rate of flow of blood through invention 100. The dimensions of the invention 100 depend in part on flow factors necessary for effective operation of the invention 100.

As depicted in FIG. 1, the two ends 21 and 23 of the chamber 1 are sealably connected to the chamber 1 perpendicularly. So long as the diameter of the chamber 1 is large enough to permit linear flow through its length, it is generally possible to have right angle corners at the end caps 21 and 23. However, end caps 21 and 23 may connect to the side of chamber 1 using a rounded corner. This rounded corner further reduces the chance for non-linear or turbulent flow. If a higher rate of blood flow through the invention 100 is desired, a rounded corner is generally more optimal than a right angle connection.

Figure 2:
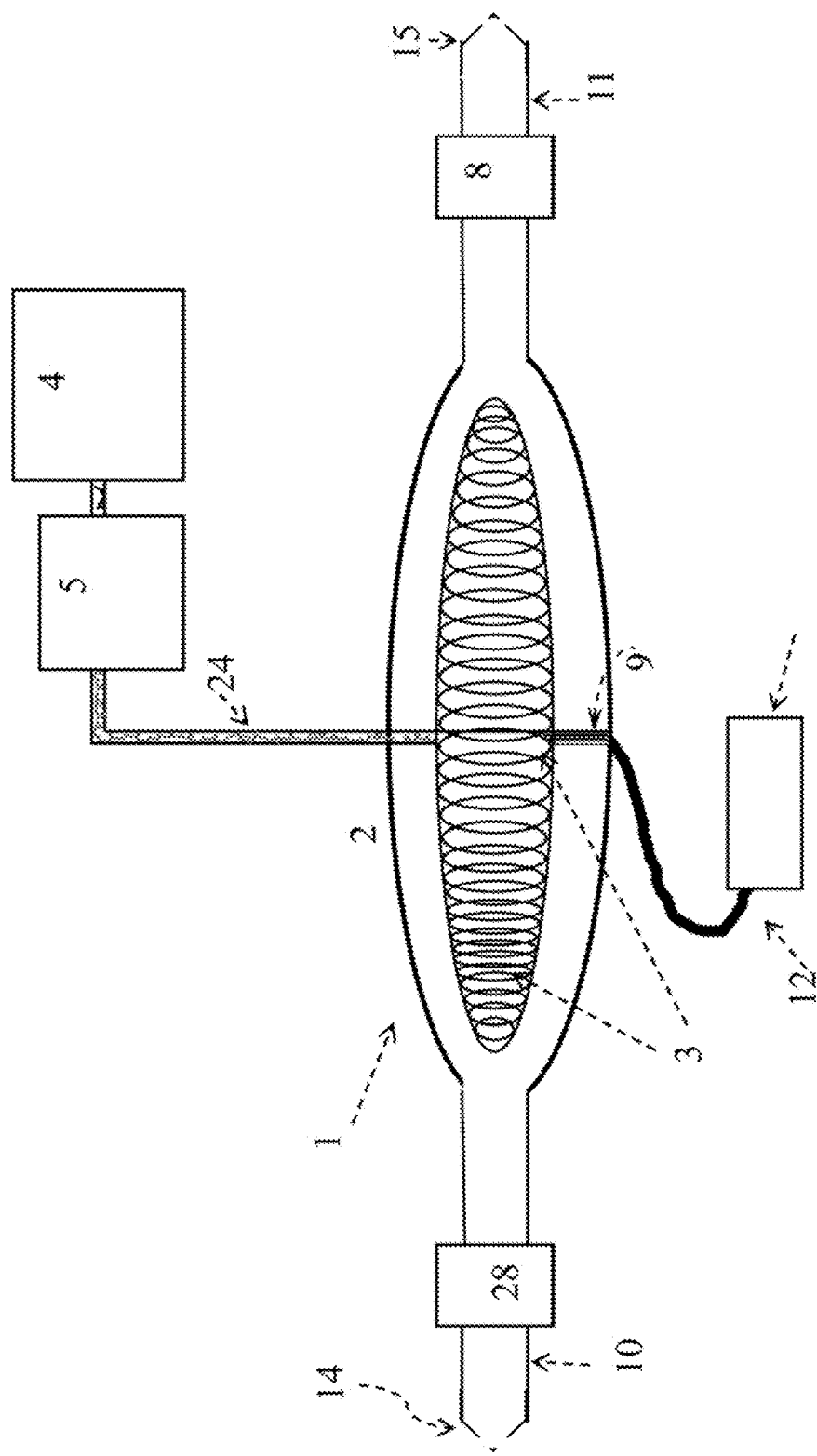
FIG. 2 depicts an alternate embodiment of the invention in which the chamber is a hollow elliptical solid shape.

In an alternate embodiment of the invention 100, and referring to FIG. 2, chamber 1 may take the form of a hollow elliptical solid-essentially the same shape as the preferred shape of the diffuser 2. For clarity, the shape of chamber 1 in this embodiment may also be referred to as a prolate spheroid or ellipsoid, that is to say, three dimensional and hollow. In this alternate embodiment, the geometry of the outer surface of diffuser 2 closely conforms to the geometry of the inner, surface of the chamber 1. As a result, the blood flow through the chamber 1 experiences minimal disruptions which might cause turbulence or non-linear flow.

Figure 5:
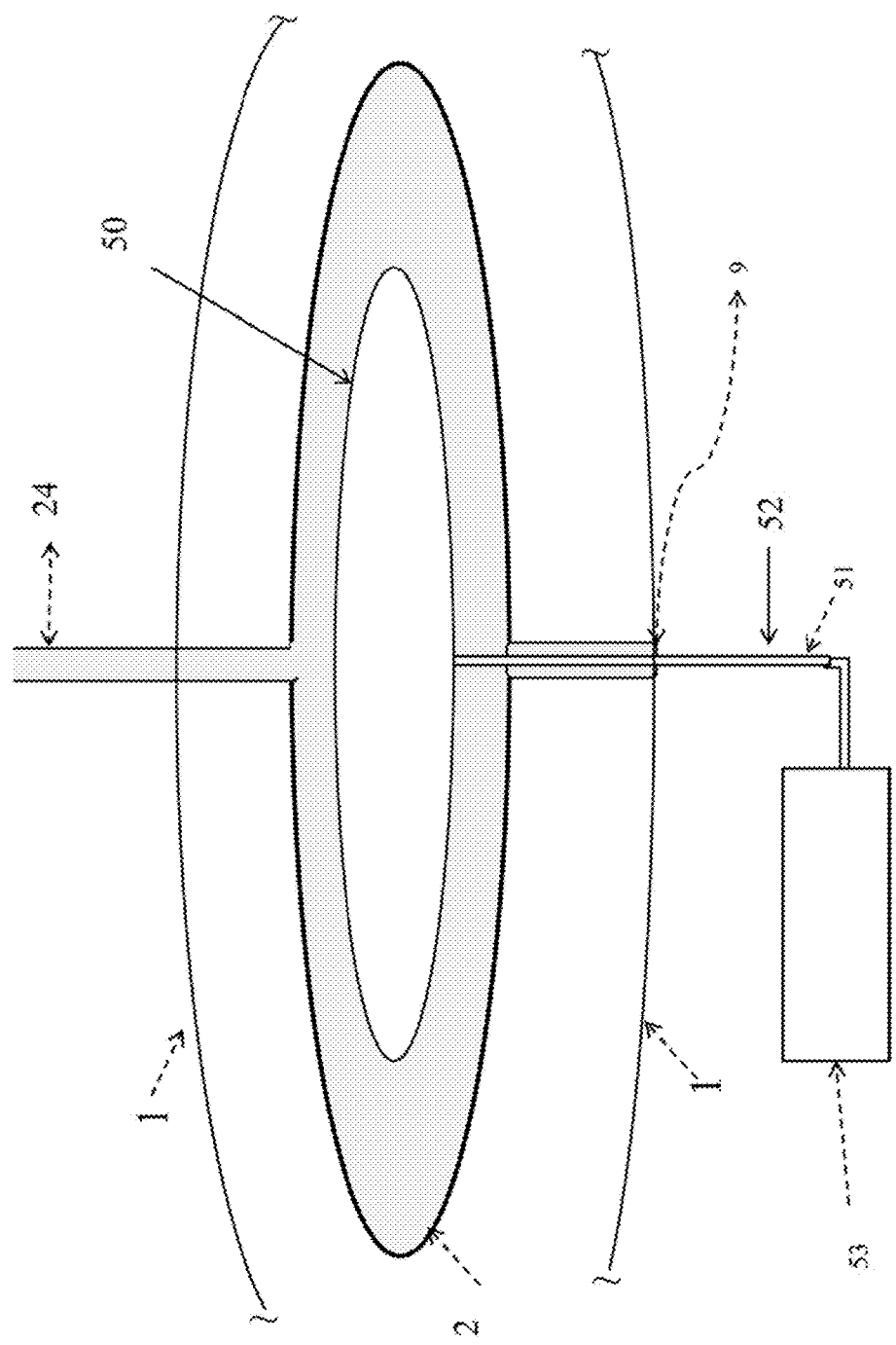
FIG. 5 depicts an alternate embodiment of the invention in which a tank of heated water acts as the heating element of the device.

Referring to each of FIG. 1 and FIG. 2, wholly contained within chamber 1 is a heating element 3 disposed along the long axis of the diffuser 2. The heating element 3 may be a helical wire element. However, any form of heating device capable of fitting within the chamber 1, in either embodiment, and heating blood to a precise and predetermined temperate between 105 degrees F. and 106.7 degree F. as blood flows the length of the chamber 1 may be used. In a preferred embodiment, heating element 3 in the form of a helical coil is disposed on the inner surface of an ozone diffuser 2, described below. The heating element 3 is constructed of a material which does not react either to chamber 1, blood or the ozone diffuser 2. Referring to FIG. 5, in an alternate embodiment, the heating element may be a reservoir 50 of hot water which is circulated via piping through and around the interior of the diffuser 2.

In each of FIG. 1 and FIG. 2, only a single, uniform helical heating element 3 is depicted. This is not a limitation. As described above, any suitable heating element, such a ribbon heating element (not depicted), disposed within or outside the ozone diffuser 2, may be used. For example and not as a limitation, a plurality of heating ribbons may be embedded in a hollow cylinder of a diameter smaller than that of chamber 1 and placed such that the longitudinal axes of each of the hollow cylinder containing the plurality of heating elements 3 and chamber 1 are congruent. In this embodiment, blood would flow outside and through the hollow cylinder for heating. The hollow cylinder embodiment requires perforation to permit ozone to be diffused through the flowing blood. How, in this embodiment, the important factor is the retention of radial symmetry to heat the blood evenly through the chamber 1.

As depicted in FIG. 8, the critical factor in thorough hyperthermia of the blood is the radial symmetry of the chamber 1 and the combination of heating element 3 (or plurality of heating elements 3) and diffuser 2. Based on flow characteristics of a fluid through a cylinder, flow of the fluid is slower at any surface, such as the interior surface of the cylinder, and faster at the center. However, the flow is radially symmetric. Any heating element 3 which heats in a radially symmetric manner may serve as a sufficient heater. Likewise, any diffuser 2 which diffuses gas in a symmetric pattern may serve as a diffuser 2. In FIG. 7, another embodiment of the heating element 3 is depicted. The heating element 3 of FIG. 7 is a solid bar 30.

The design of the chamber 1 is such that the rate of blood flow through the chamber 1 is sufficiently long, in terms of time, as to ensure uniform heating of the blood and all blood components along the heating coil 3 to the necessary temperature while ensuring accurate control of the temperature of the blood throughout chamber 1. The heating coil 3 is controlled by a regulator 7 and power supply 6, each also depicted in FIG. 1. No specific dimensions of chamber 1 are indicated. In the event a slower hyperthermia cycle is indicated, a longer chamber 1 and longer heating element 3 are required. The primary factors which determine the size of various parts of the invention 100 include the amount of blood to be treated, the temperature or temperatures to which the blood is raised, whether simultaneous or independent hyperoxygenation is performed, the amount of time the blood remains as the desired temperature. All of these elements, of course, depend on the underlying disease the patient has.

Thus, while a single heating element 3 is depicted in FIG. 1, this is not a limitation. Although it is necessary to maintain radial symmetry of the heating element 3 along the long axis of the chamber 1, in some embodiments it may be useful to provide a plurality of heating elements 3, each controlled by a separate regulator 7 (although wiring techniques may permit a shared power supply 6). A plurality of heating elements 3 would permit heating gradients to be imposed along die length of the chamber 1. For example, a higher temperature heating element 3 at the upstream end of the flow of blood in the chamber 1, with reduced temperature heating elements (one or more) 3 downstream would result in blood subjected to rapid temperature rise following by slower additional temperature rise. In another embodiment, a rising temperature gradient could be imposed using a plurality of heating elements 3 along the flow of blood through the chamber 1. The use of a plurality of individually controlled heating elements, which might include gaps between any two to permit some cooling of the blood, permits precise temperature control as the blood is heated, including the length of time the blood remains at a desired temperature.

As further depicted in FIG. 1, an off-the-shelf, commercially available ozone source (not depicted) is employed to contain or produce a supply of high concentration ozone, which is then disposed into an ozone supply 4 connected to the diffuser 2 via an ozone connection tube 24 for infusion of ozone into the blood. Ozone pressure in the diffuser 2 is controlled by a pressure regulator 5.

As with the heating element 3, the ozone diffuser 2 is placed in the chamber 1 in a radially symmetry manner. As depicted in FIG. 1, in a preferred embodiment, the ozone diffuser is an elongate, hollow elliptical solid. The cross-section of the diffuser 2 matches, the cross-section of the chamber 1, as depicted in FIG. 6 and FIG. 8. The outer surface of the ozone diffuser 2 imposes another fluid flow boundary condition. However, the elongate, elliptical shape of the ozone diffuser 2 minimizes any disruption to blood flow. The outer surface of the diffuser 2 may also have a low friction coating applied to it. Referring to FIG. 6 and FIG. 8, the radial symmetry of such a diffuser 2 shape within the hollow cylinder comprising the chamber 1, when mated to the cross-section of the chamber 1, reduces the likelihood of turbulent or non-linear flow. However, in the preferred embodiment, an operator of the invention 100 must be aware of the increase of blood flow rate as the flow approaches the widest (radially) part of the ozone diffuser 2 and the concomitant slowing of blood flow as blood flows past the narrower part of the ozone diffuser 2. This issue is not significant in the alternate embodiment of FIG. 2, in that the shape of chamber 1 closely conforms to the shape of the diffuser 2 along the entire length of the diffuser 2.

Figure 3:
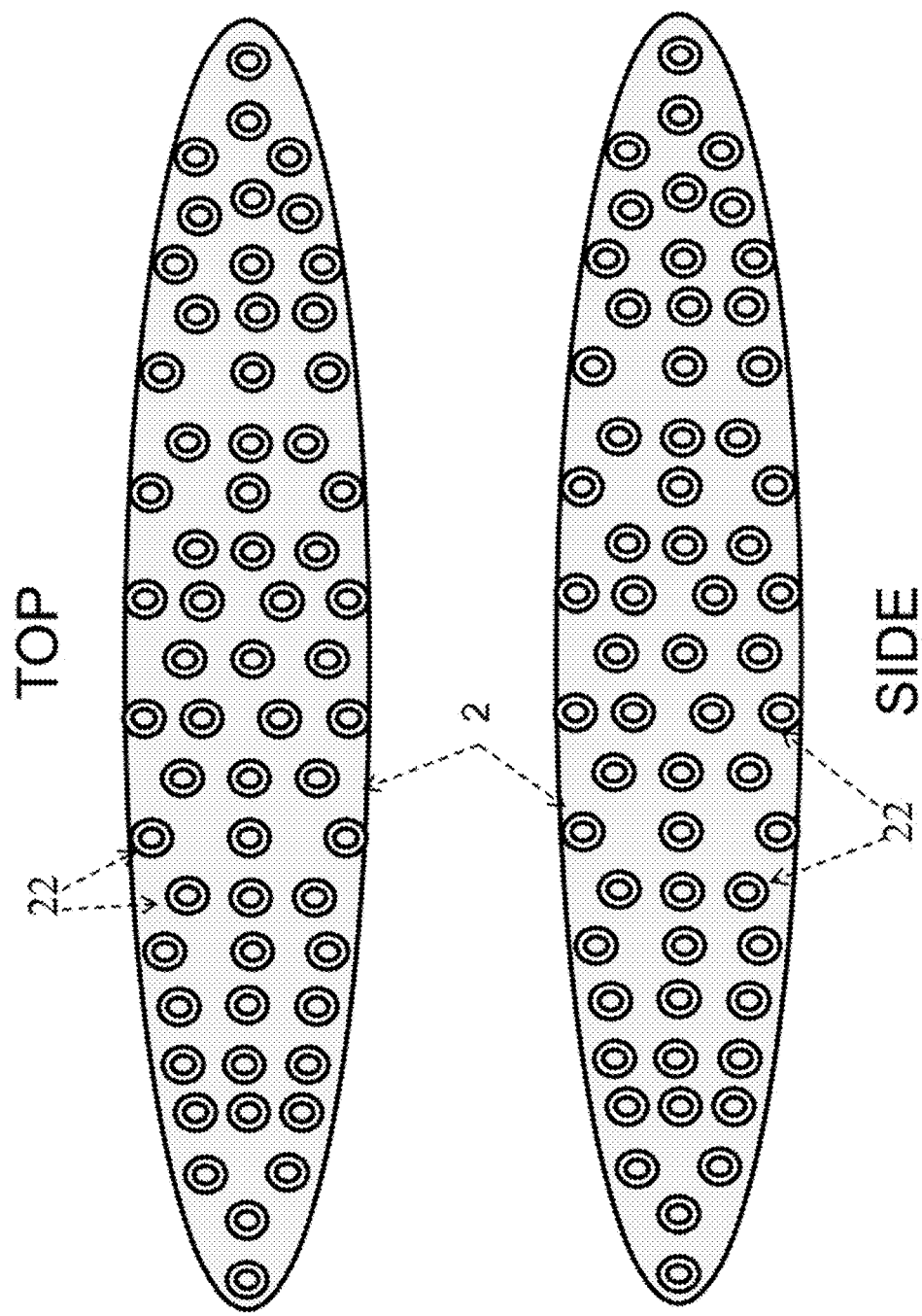
FIG. 3 depicts a top and side view of the preferred diffuser of the invention with ozone pores.

Referring now to FIG. 3, the ozone diffuser 2 is ideally an elliptical solid in shape and hollow. The form of the diffuser 2 is such that, in an embodiment, it is disposable within a helical form of heating element 3. If the heating element 3 is placed on the outer surface of diffuser 2, the diameter of the wire forming the heating element 3 must be small enough not to disrupt the flow of blood. In alternate embodiments, the heating element 3 or plurality of heating elements 3 are disposed within the diffuser 2. Upon the surface of the diffuser 2 are disposed a plurality of pores 22 along the entire surface. The number and size of pores is determined by level of ozone or oxygen saturation required or desired. So long as the heating element 3 is suitably shaped to accommodate the pores 22 of the ozone diffuser b, heating elements 3 (one or more) may be disposed inside or outside the ozone diffuser 2. The only other significant limitation is the need to maintain radial symmetry.

Figure 4:
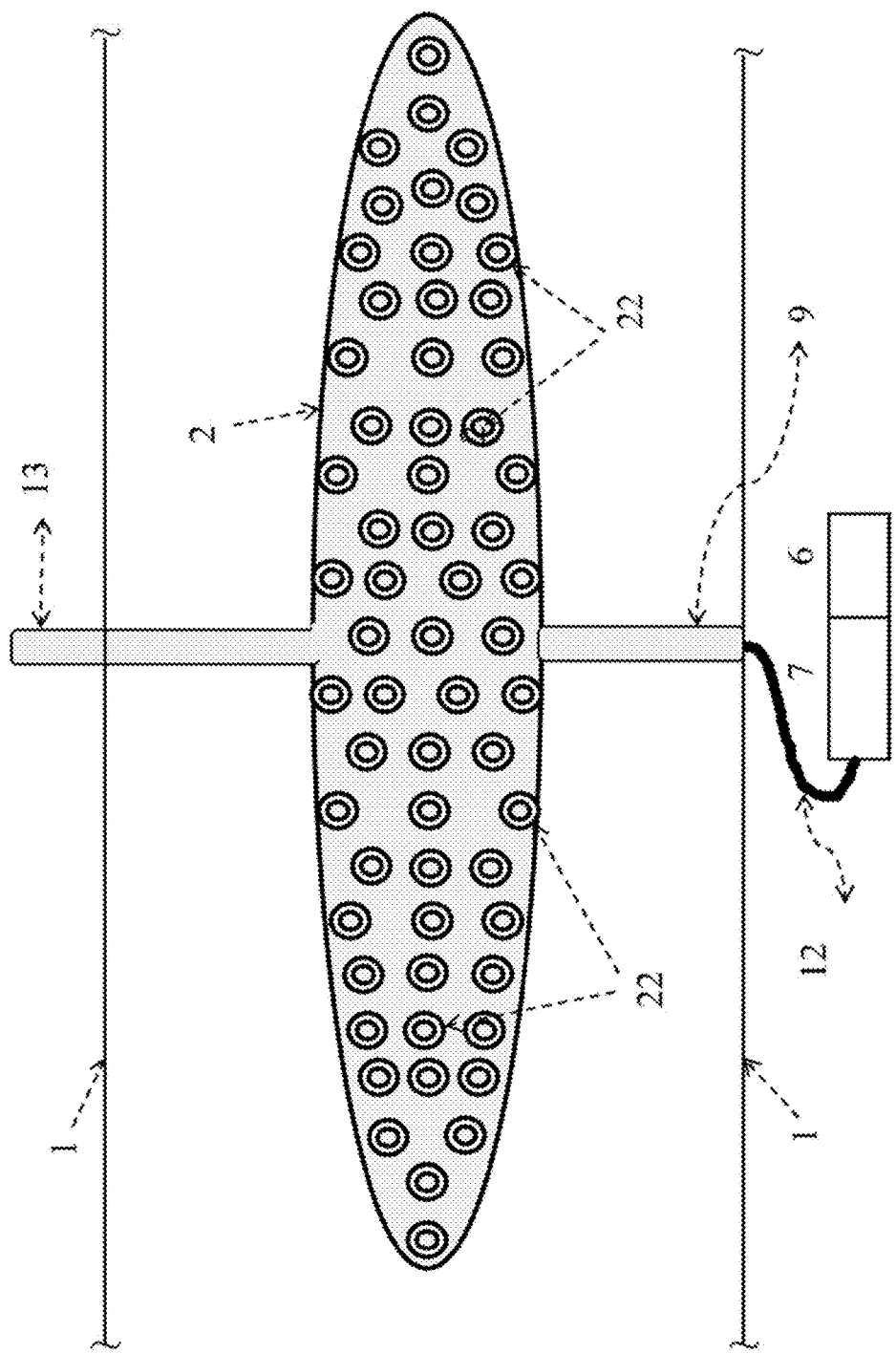
FIG. 4 depicts a side view of the position of the preferred embodiment of the diffuser in the preferred embodiment of the chamber.

Referring now to FIG. 4, ozone is infused into the blood via pressure differentials created by the pores 22 which disperse the ozone uniformly across the blood flow through the ozone diffuser 2 within chamber 1. Ozone not absorbed into the blood is vented from the chamber 1 via a vent 13. The diffuser 2 is mounted within the chamber 1 upon one or more support columns 9. The support columns 9 are of sufficiently small diameter and shape so as to prevent interference with blood flow and to prevent the formation of eddies, turbulence or other nonlinear flow.

Still referring to FIG. 4, at least one support column 9 is hollow. This allows a power cable 12 to be run into the diffuser 2 to power the heating element 3. In the event one or more heating elements 3 is not in contact with the ozone diffuser 2, a separate, small diameter column must be run into the chamber 1 to power each of the one or more heating element 3. If more than one heating element 3 is used, a plurality of power cables 12 may be used. Column 13 is hollow to allow passage of a gas from its supply.

FIG. 1 and FIG. 2 each depict a single ozone diffuser 2. Although the invention 100 includes a minimum of one diffuser 2 capable of diffusing some hyperoxygenating gas into the blood, other embodiments allow a plurality of diffusers 2 to be disposed in the chamber 1. As with the optional plurality of heating elements 3, the primary limitations on the number and placement of ozone diffusers 2 are the equal needs to maintain radial symmetry and assume linear flow. In the event multiple diffusers 2 are used, it is equally permissible to use a plurality of beneficial gasses. For example, ozone ($O_3$) might be used in conjunction with oxygen ($O_2$). Although some human cells, such as lung cells, may be harmed by the presence of ozone, it is generally considered medically that over-saturating blood with oxygen or ozone is not harmful to the patient and poses no medical threat or risk.

The outer surface of the ozone diffuser 2 may be coated with a low friction material to reduce interaction with the flow of blood over the ozone diffuser 2. In the event a plurality of ozone diffusers 2 are used, a low friction coating may be used with one or more of the plurality of ozone diffusers 2 depending on the desired flow characteristics sought proximate to each.

Although the ozone diffuser 2 depicted in FIG. 3 is described as being hollow, a hollow ozone diffuser 2 is suitable where the pressure applied to the gas diffused into the blood is sufficient to prevent the incursion of blood into the diffuser 2. In applications in which the gas pressure is too low to accomplish this, an alternate embodiment of the ozone diffuser 2 is a solid body elliptical or other radially symmetric diffuser 2 with pores 22 connected to an ozone supply 4 via small connecting holes drilled or otherwise disposed into the body of the solid ozone diffuser 2. In yet another embodiment, a network of small tubes may be disposed on the surface of the solid ozone diffuser 2. The small tubes then connect to the pores 22 of the ozone diffuser 2.

Referring to either FIG. 1 or FIG. 2, the pressure applied to the hyperoxygenating gas by the pressure regulator 5 must be sufficient to impose radial symmetry in the diffusion of gas through the blood. Any gas is naturally buoyant in a fluid, such as blood. This makes it more difficult to diffuse ozone or other hyperoxygenating gas to the downward side of the chamber 1 because buoyancy works against diffusion on the downward side. In this disclosure, the "downward" side is simply the side which is toward gravity and away from an "up" or skyward direction. Buoyant forces act toward the up side and against the down side. Because of this, any gas diffused into the blood will move to a higher concentration in the up side of the chamber 1 and in a lower concentration on the down side of the chamber 1. To account for this, pores 22 on the downward side of a hollow diffuser 2 may be larger to permit a larger amount of gas to be diffused. A gradient of pore 22 sizes (smaller at the top of the diffuser 2 and larger at the bottom) may be imposed on the surface of the diffuser 2. In a solid diffuser 2 or if a plurality of diffusers 2 are used, a plurality of pressure regulators 5 may be used to impart different pressures of diffused gas to different positions on the diffuser 2 or diffusers 2 to counteract buoyancy and impose equal diffusion radially in the chamber 1.

Keeping in mind the lack of general harm in over-diffusing ozone or other beneficial gas, it is equally permitted to regulate the pressure of the ozone or other gas to be diffused to provide sufficient diffusion to the blood in all parts of chamber 1. Hyperoxygenation may be accomplished sufficiently if the operator of the invention 100 supplies enough ozone or other therapeutic gas so as to hyperoxygenate the blood at the far downward side of the chamber 1. All other locations in the chamber 1 will receive a superabundance of the therapeutic gas, but not a harmful amount.

The length of chamber 1 is determined primarily by the need to impart sufficient heating uniformly to the blood. To some extent, the length of the chamber 1 is determined by the amount and rate of gas diffusion desired. In either case, the structure of the invention 100 is determined primarily by what is needed to kill pathogens or cancer cells while maintaining the health and/or normalcy of the remainder of blood components. For example, it may be effective to kill a certain virus by raising its temperature to 105 degrees F., maintaining that temperature (or lowering it) and then raising the temperature to 106 degrees F. In another embodiment, it may be optimal to kill pathogens by subjecting them to an alternating application of heat, then ozone, then heat, then ozone. These examples are not limiting. In alternate embodiments, any combination of heat or ozone, together or serially, at different temperatures, pressures or types of gas may be imposed within the invention 100.

Referring to FIG. 1 and FIG. 2, the treated blood exits the chamber 1 through an outlet placed at the opposite end of chamber 1 from connecting tube 10. The outlet is identified in FIG. 1 as connecting tube 11. A variable speed pump 8, which must not harm any blood components, may be used to regulate flow at, the outlet. The blood may then be returned to the patient via a return tube connected to nipple 15 and back into the patient's body and internal circulatory system or stored for later return.

The approach to the use of the invention is: 1) to use a maximum ozone concentration and predetermined temperature to kill harmful cells or viruses, while improving the rheology and biochemical characteristics of blood components, causing minimal damage to them, and 2) to minimize blood cell damage during ozone saturation and hyperthermia treatment. Further, the procedure is designed to expose autologous blood to ozone and high temperatures sufficient to kill or weaken disease-causing viruses, cells or pathogens, but not so high that it damages or kills blood components (106.7 degrees F. is generally agreed to be the maximum temperature to which human blood cells can be exposed), followed by reinfusion in patients affected by diseases or cancer. The hyperoxygenation and hyperthermia of the blood returned to the body produces additional therapeutic results in vivo.

In the preferred embodiment, the electrical heating system for the heating element 3 consists of a basic AC/DC power supply unit attached to the ends of a heating element 3 on or in the diffuser 2 in a helical fashion so as to distribute the heating uniformly over the surface of the diffuser 2. As described above, in other embodiments the heating element 3 may take any shape suitable to fit within the chamber 1 that does not disrupt the flow of blood and which can heat in a radially symmetric pattern.

In addition to the alternative heating elements 3 described above and now referring to FIG. 5, heating of the blood may also be accomplished by the use of heated water piped into a reservoir 50 disposed in the diffuser 2. Hot water is pumped into the reservoir 50 through a supply line 51. Similarly, a coiled tube of water (not depicted) in the manner of a radiator may be placed within the diffuser 2. The supply line 51 further comprises an integrated water return line 52.

This permits the hot water to be continuously replenished. The water supply is pumped by a standard pump 53.

In the preferred embodiment, and referring to FIG. 1, the power cable 12 supplying current to the heating, element 3 enters the diffuser 2 ellipsoid from the power supply 6 and regulator 7 through the support tube 9 penetrating the wall of the chamber 1, and is attached to the heating element 3 in the interior surface of the diffuser 2 ellipsoid in a helical fashion so as to distribute heating uniformly over the surface of the diffuser 2.

Still referring to FIG. 1, each support tube 9 is of sufficiently small diameter and geometry as to prevent the creation of turbulence or other non-linear flow characteristics. Generally, support tube 9 is a long, thin circular cylinder. In some applications of the invention 100, however, the flow of blood through chamber 1 may be fast enough that a circular cylinder of any sufficient size to support the diffuser 2 may still cause turbulence or other non-linear flow characteristic. In that case, an elliptical cylindrical design for the support tube 9 may be used. In that case, the long axis of the elliptical cylindrical support tube 9 is oriented to lie parallel to the direction of blood flow, thus reducing turbulence or non-linear flow.

Heating within the chamber 1 is controlled and regulated by a current regulator 7 to achieve a blood temperature of at least 105 degrees F., and maintained within, the temperature range of 105 degrees to a maximum of 106.7 degrees F. within the chamber 1. One or more thermometers, of a design and with operational capabilities known in the industry, may be incorporated into the body of the chamber 1 along, its length to measure the temperature of the blood in the invention at various locations.

Having heated the blood to a controlled temperature of at least 105 degrees F., the blood is simultaneously oxygenated with a high concentration of ozone ($O_3$) to a specified level of concentration regulated by a regulator 5. The ozone is infused into the blood through the plurality of pores 22 on the surface of the diffuser 2 by pressure differential created within the interior of the diffuser 2, and dispersed via pressure through the plurality of pores 22.

Blood is returned to the patient's circulatory system oxygenated and heated. In an alternate embodiment, the blood is cooled to body temperature prior to return to the patient.

In an alternate embodiment, the invention 100 may be an effective means of delivering other cancer fighting agents to the patient in addition to or other than ozone and oxygen by changing the ozone supply to an optional cancer fighting agent supply system.

In an alternate embodiment, the invention 100 may be used to treat illnesses and conditions in non-human animals, with temperatures and oxygen saturation levels scaled to allow for the needs of the individual animal so treated.

The invention 100 can be made in different sizes and dimensions to whatever scale (large or small) is necessary to accomplish its intended function and purpose. In an alternate embodiment, the invention may be used to sterilize stored blood. Sterilization of blood supplies may require a larger scale device than one used for individual human or animal treatments. Consequently, the design of the device enables homogeneous heating and oxygen/ozone mixing with the possibility of fabricating the device at variable dimensions and scales.

The invention 100 as described is portable. As such, it is usable away from hospital environments and treatment centers, and so may have tremendous use and application in the home care industries, ambulances as well as military battlefield environments. It is especially useful for transportation to and use at blood storage facilities.

I claim:

1. A device for hyperoxygenation-hyperthermia treatment comprising
    a blood inlet;
    a blood outlet;
    a chamber in the shape of a prolate spheroid;
    a gas diffuser in the shape of a prolate spheroid;
    and a heating element in the shape of a prolate spheroid
    wherein the blood inlet is positioned at the first end of the chamber along the major axis of the chamber,
    and the blood outlet is positioned at a second end of the chamber along the major axis of the chamber
    wherein the gas diffuser and heating element are within the chamber
    and wherein the major axis of each of the chamber, the gas diffuser and the heating element are coaxial.

2. The device of claim 1 in which the device comprises a plurality of heating elements combined in the shape of a single prolate spheroid.

3. A device for hyperoxygenation-hyperthermia treatment comprising
    a blood inlet;
    a blood outlet;
    a chamber in the shape of a prolate ellipsoid;
    a gas diffuser in the shape of a prolate ellipsoid;
    and a heating element in the shape of a prolate ellipsoid
    wherein the blood inlet is positioned at the first end of the chamber along the major axis of the chamber,
    and the blood outlet is positioned at a second end of the chamber along the major axis of the chamber
    wherein the gas diffuser and heating element are within the chamber
    and wherein the major axis of each of the chamber, the gas diffuser and the heating element are coaxial.

4. The device of claim 3 in which the device comprises a plurality of heating elements combined in the shape of a single prolate ellipsoid.

* * * * *